United States Patent [19]

Omoigui

[11] Patent Number: 5,095,896

[45] Date of Patent: Mar. 17, 1992

[54] AUDIO-CAPNOMETRY APPARATUS

[76] Inventor: Sota Omoigui, 8501 Millicent Way, Apt. 2139, Shreveport, La. 71115

[21] Appl. No.: 727,965

[22] Filed: Jul. 10, 1991

[51] Int. Cl.5 .......................................... A61M 16/00
[52] U.S. Cl. ......................... 128/200.26; 128/205.23; 128/207.14
[58] Field of Search ..................... 128/202.22, 205.23, 128/207.14, 207.15, 200.26, 719

[56] References Cited

U.S. PATENT DOCUMENTS

| | | | |
|---|---|---|---|
| 2,638,096 | 5/1953 | Waldhaus | 128/207.14 |
| 3,000,377 | 9/1961 | Tolbert et al. | 128/719 |
| 4,344,436 | 8/1982 | Kubota | 128/207.15 |
| 4,416,289 | 11/1983 | Bresler | 128/207.14 |
| 4,431,005 | 2/1984 | McCormick | 128/207.14 |
| 4,445,501 | 5/1984 | Bresler | 128/207.14 |
| 4,485,822 | 12/1984 | O'Connor et al. | 128/719 |
| 4,537,190 | 8/1985 | Caillot et al. | 128/205.23 |
| 4,648,396 | 3/1987 | Raemer | 128/719 |
| 4,738,266 | 4/1988 | Thatcher | 128/719 |

Primary Examiner—Edgar S. Burr
Assistant Examiner—Aaron J. Lewis
Attorney, Agent, or Firm—Rod Bryant Jordan

[57] ABSTRACT

An apparatus for use in audio monitoring of carbon dioxide concentration in general, and as an aid in blind nasal intubation, as well as other procedures requiring the monitoring of carbon dioxide in which carbon dioxide is measured by a carbon dioxide monitor, the carbon dioxide monitors output is used as the control voltage of a voltage controlled oscillator, and the output of the voltage controlled oscillator is amplified, delivered to a speaker, and thereby produces an audible tone whose pitch is directly proportional to the level of carbon dioxide being monitored.

3 Claims, 2 Drawing Sheets

AUDIO-CAPNOMETRY APPARATUS

BACKGROUND OF THE INVENTION

The present invention relates to an apparatus for use in audio monitoring of carbon dioxide. The present invention can be used in administering anesthesia as well as in any situation where carbon dioxide is being monitored. One of the uses for the present invention in anesthesia will be in the process of blind nasal intubation. This process is often elected for use in intraoral operations when anatomic abnormalities or disease of the upper airway make direct laryngoscopy difficult, or in order to facilitate long term intubation of the lungs.

DESCRIPTION OF THE PRIOR ART

In cases requiring intubation, where direct laryngoscopy is impractical, the physician must rely upon blind or fiberoptic intubation. The flexible fiberoptic bronchoscope is, however, often unavailable, especially in emergency situations. In addition, the presence of blood and secretions, and their effect upon the field of vision, often leaves blind intubation the method of choice.

In the process of blind intubation, the mucosa is anesthetized and constricted in order to ensure maximum patient comfort, nasal patency, and to minimize the chance of epistaxis associated with nasotracheal intubation. This being accomplished, the endotracheal tube is passed through the nares into the oropharynx and advanced toward the glottic opening. Formerly, in order to proceed correctly the physician was required to listen for maximal breath sounds being exhausted from the end of the endotracheal tube. This required that the end of the tube be in close proximity to the physician ear, further complicating a tedious task. Other methods of guidance in blind intubation that have met minimal success are: observance of condensation within the endotracheal tube, use of a suction catheter, electronically magnifying the breath sounds, and observing inflation of the cuff. Shortcomings in these methods, such as difficulty in hearing breath sounds and contamination by body secretions, have brought reliance upon what is now considered the most effective method of endotracheal tube guidance, that being the monitoring of the end-tidal carbon dioxide.

Based on the logical postulate that the concentration of carbon dioxide in the oropharynx is maximal at the glottis during expiration, the endotracheal tube may be guided to its proper placement by periodically sampling the gases within the endotracheal tube, measuring the carbon dioxide concentration through the use of a carbon dioxide monitor and displaying the level of concentration on a capnograph. There is, however, one serious problem with this most reliable method of blind intubation. The need to look up at the carbon dioxide waveform as displayed on the capnograph provides a major distraction at a time when maximum concentration is required. The introduction of the invention as described herein will eliminate this problem. The herein described invention has been tested and has shown great promise as a major advancement not only in blind nasal intubation, but also in audio monitoring of carbon dioxide.

SUMMARY OF THE INVENTION

The invention consists of a carbon dioxide monitor, whose output is coupled to a voltage controlled oscillator, whose output is in turn amplified and delivered to a speaker. As earlier noted, one use for the invention is that of aiding a physician in the process of blind nasal intubation. In this procedure the carbon dioxide monitor is coupled to an endotracheal tube having a gas sampling port. The gas within the tube is periodically sampled in order to determine the level of carbon dioxide so that the physician may monitor the carbon dioxide audibly and thereby guide the endotracheal tube to the glottis, as previously explained. The output of the carbon dioxide monitor, however, is delivered to the input of a voltage controlled oscillator, as well as to the capnograph. The amplitude of the voltage produced by the carbon dioxide monitor varies with the level of carbon dioxide. Therefore, the output frequency of the voltage controlled oscillator varies in direct proportion to the level of carbon dioxide as sampled at the sampling port of the endotracheal tube. The output of the voltage controlled oscillator is then delivered to an amplifier-speaker system, thus producing an audible tone whose frequency, or pitch, is also in direct proportion to the concentration of carbon dioxide at the sampling port of the endotracheal tube. The physician may then guide the endotracheal tube to the glottis, eventually discovering the optimum position in a "warmer-colder" manner by listening to the tone produced by the speaker, knowing that the optimum position of the endotracheal tube will result in the highest pitch sound. The presence of a high pitch sound indicates that the endotracheal tube is near the glottis. An increase in pitch indicates that the endotracheal tube is moving toward the glottis and a sudden decrease in pitch indicates that the endotracheal tube is being misdirected, allowing for immediate correction. The entire process may therefore be completed more safely and efficiently due to the fact that the physician need never remove his eyes or his complete attention from the patient.

The equipment and procedure as described have many advantages over other methods of blind intubation. Advantages include ease of operation, minimal risk of contamination by body secretions, immediate confirmation of appropriate placement of the endotracheal tube, and the fact that oxygen may be administered during the procedure through the nasotracheal tube. The equipment, though prodigious in its own right as an aid to blind intubation, may conceivably be adapted to other procedures such as fiberoptic bronchoscopy, routine (visual) intubation, and audio monitoring of carbon dioxide during anesthesia.

BRIEF DESCRIPTION OF DRAWINGS

FIG. one is a picture-block diagram of the Audio Capnometry Apparatus.

FIG. two is a typical voltage controlled oscillator circuit suitable for use in the Audio Capnometry Apparatus.

DETAILED DESCRIPTION OF THE INVENTION

Figure 1:
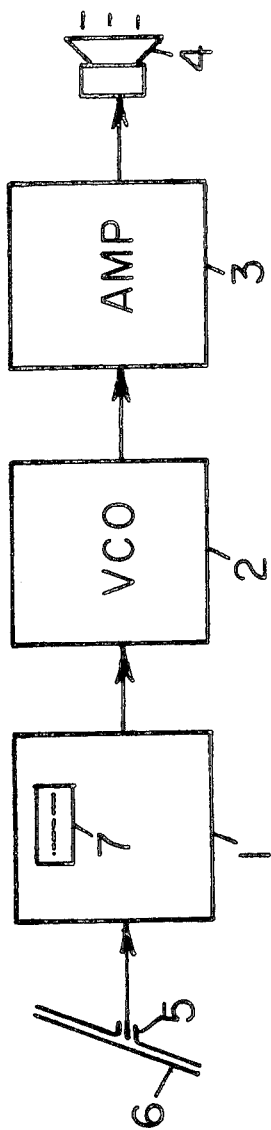
Figure 2:
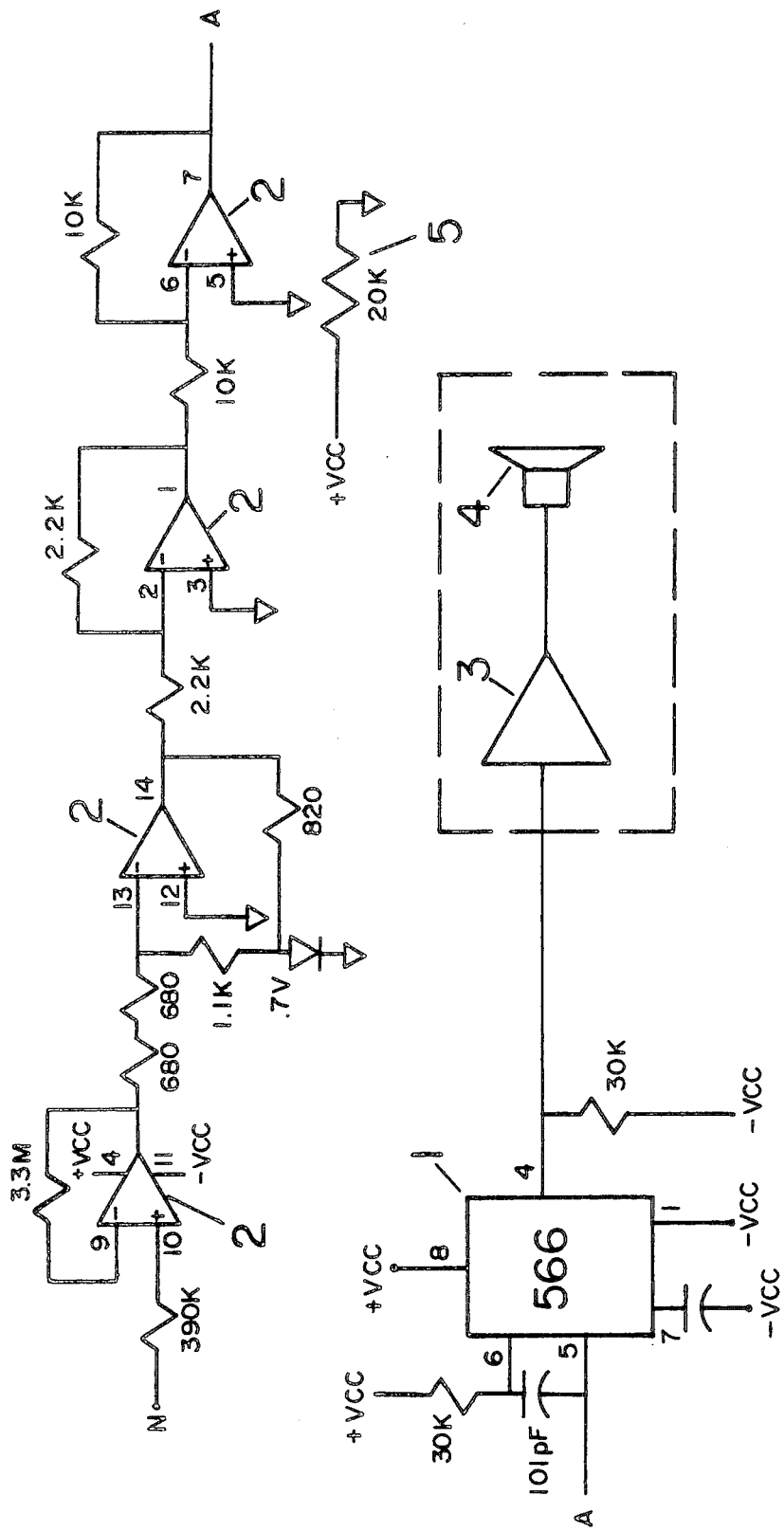

Referring to the drawings, and more specifically to figure one, it can be seen that the audio-capnometry apparatus comprises essentially a carbon dioxide monitor 1, whose analog output DC voltage is delivered to a voltage controlled oscillator 2, whose output oscillation or AC voltage is in turn delivered to an audio amplifier 3, whose output AC voltage is then directed to a speaker 4. The frequency of the oscillator 2 is tuned within the audible range so that the speaker 4 will produce an audible tone. The carbon dioxide monitor 1 is coupled to the sampling port 5 of an endotracheal tube 6. The carbon dioxide monitor 1 periodically samples the carbon dioxide level within the endotracheal tube. The analog output of the carbon dioxide monitor comprises a DC voltage whose amplitude is directly proportional to the carbon dioxide level within the endotracheal tube 6. The DC output of the carbon dioxide monitor is then delivered to the input of the voltage controlled oscillator 2, as well as to the capnograph 7. As the DC voltage supplied to the voltage controlled oscillator 2 is varied, the frequency of the output AC voltage of the oscillator varies in direct proportion to the amplitude of the DC input voltage, and, therefore, also to the carbon dioxide level within the endotracheal tube 6. This audio output AC voltage is then amplified by the amplifier 3, and sent to the speaker 4, inducing the speaker to produce an audible tone whose pitch is in direct proportion to the level of carbon dioxide within the endotracheal tube.

Referring to figure two, it can be seen that the voltage controlled oscillator comprises a voltage controlled oscillator integrated circuit chip 1, and a series of buffer amplifiers 2, along with various support circuitry. The output voltage of the carbon dioxide monitor (not shown) is delivered to the first buffer amplifier 2. The final buffer amplifier inverts the voltage and delivers it as a control voltage to the oscillator chip 1. The control voltage thus varies in direct proportion to the carbon dioxide level as measured by the carbon dioxide monitor. The output of the voltage controlled oscillator chip 1 is then delivered to an audio amplifier 3, and on to a speaker 4, resulting in an audible tone whose pitch varies in direct proportion to the carbon dioxide level as measured by the carbon dioxide monitor. The potentiometer 5 may be set to a desired threshold voltage so as to avoid the continual production of the audible tone.

CONCLUSION

The placement of endotracheal intubation tubes, as previously discussed, is often accomplished through visual or blind intubation. The procedure of blind intubation as accomplished by the afore described method, through the use of the above described audio capnometry device, provides medical practitioners with a new, invaluable advancement in the placement of endotracheal intubation tubes. Visual intubation may also be facilitated by the audio capnometer which signals an immediate confirmation of correct placement of the endotracheal tube. At present, the person performing the intubation must frequently glance at the carbon dioxide monitor for confirmation. With the Audio Capnometer, they will hear the pitch immediately. In addition, carbon dioxide monitoring during anesthesia can be accomplished audibly, therefore, abnormalities in the carbon dioxide wave form will be more easily detected through the use of the Audio Capnograph.

I claim:

1. An apparatus for audio monitoring carbon dioxide concentration comprising, a carbon dioxide monitor said monitor so arranged as to measure said concentration of carbon dioxide, said carbon dioxide monitor having an output DC voltage, said output DC voltage having a varying amplitude, said amplitude being representative of said concentration of said carbon dioxide being measured, a voltage controlled oscillator, said oscillator having a control voltage, said control voltage further comprising said output DC voltage, said oscillator being capable of producing oscillations, said oscillations further comprising an AC voltage, said AC voltage having a specific frequency, said frequency being determined by said varying amplitude of said control voltage, an audio amplifier, said amplifier, having an input and an output, said amplifier so connected to said voltage controled oscillator so as to utilize said AC voltage as said input, said output further comprising an amplified representation of said AC voltage, and a speaker, said speaker so connected to said amplifier so as to receive said output, there by producing an audible tone, said audible tone having a varying pitch, said pitch being representative of said concentration of carbon dioxide being measured.

2. An apparatus for audio monitoring carbon dioxide concentration during intubation comprising, an endotracheal tube, said tube further comprising a sampling port, a carbon dioxide monitor, said monitor so arranged as to measure said concentration of carbon dioxide at said sampling port, said carbon dioxide monitor having an output DC voltage, said output DC voltage having a varying amplitude, said amplitude being representative of said concentration of said carbon dioxide being measured, a voltage controlled oscillator, said oscillator having a control voltage, said controll voltage further comprising said output DC voltage, said oscillator being capable of producing oscillations, said oscillations further comprising an AC voltage, said AC voltage having a specific frequency, said frequency being determined by said varying amplitude of said control voltage, an audio amplifier, said amplifier, having an input and an output, said amplifier so connected to said voltage controled oscillator so as to utilize said AC voltage as said input, said output further comprising an amplified representation of said AC voltage, and a speaker, said speaker so connected to said amplifier so as to receive said output, there by producing an audible tone, said audible tone having a varying pitch, said pitch being representative of said concentration of carbon dioxide as sampled at said sampling port of said endotracheal tube.

3. A process of performing blind nasal intubation on a patient having a nasal passage, an oropharynx, and a glottis comprising the steps of:
  a. inserting an endotracheal tube, said tube having a sampling port, into the nasal passage, toward the oropharynx and on to the glottis,
  b. arranging a carbon dioxide monitor having a DC voltage output so as to measure the concentration of carbon dioxide at said sampling port,
  c. applying said DC voltage output to a voltage controled oscillator, amplifier, speaker arrangement so as to produce an audible tone, said tone having a frequency of pitch that is representative of said carbon dioxide being measured at said sampling port; and
  d. advancing said endotracheal tube toward and directing it to the glottis by observing said pitch of said audible tone, utilizing the obvious postulate that the concentration of carbon dioxide will be maximum at the glottis during expiration.

* * * * *